(12) United States Patent
Mitsudo et al.

(10) Patent No.: US 8,740,967 B2
(45) Date of Patent: Jun. 3, 2014

(54) STENT

(75) Inventors: Kazuaki Mitsudo, Okayama (JP);
Takayuki Kito, Kanagawa (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 0 days.

(21) Appl. No.: 13/113,429

(22) Filed: May 23, 2011

(65) Prior Publication Data

US 2011/0295360 A1    Dec. 1, 2011

(30) Foreign Application Priority Data

May 26, 2010    (JP) .................................. 2010-120455

(51) Int. Cl.
*A61F 2/06*    (2013.01)
(52) U.S. Cl.
USPC ........................................................ 623/1.15
(58) Field of Classification Search
USPC ............................... 623/1.11, 1.12, 1.15, 1.16
See application file for complete search history.

(56) References Cited

U.S. PATENT DOCUMENTS

| | | | | |
|---|---|---|---|---|
| 5,922,020 A | * | 7/1999 | Klein et al. ................... | 623/1.15 |
| 7,029,492 B1 | * | 4/2006 | Mitsudou et al. ............ | 623/1.15 |
| 8,221,489 B2 | * | 7/2012 | Issenmann et al. .......... | 623/1.15 |
| 2005/0125051 A1 | * | 6/2005 | Eidenschink et al. ....... | 623/1.12 |
| 2008/0215135 A1 | * | 9/2008 | Seguin et al. ................ | 623/1.35 |

FOREIGN PATENT DOCUMENTS

| | | |
|---|---|---|
| EP | 0 974 314 A2 | 1/2000 |
| EP | 1 034 751 A2 | 9/2000 |
| EP | 1 523 959 A2 | 4/2005 |
| JP | 2000-316983 A | 11/2000 |
| WO | WO 2006/060534 A1 | 6/2006 |

OTHER PUBLICATIONS

Extended European Search Report issued on Jul. 19, 2011 by the European Patent Office in corresponding European Patent Application No. 11 16 6191.

* cited by examiner

*Primary Examiner* — Tuan V Nguyen
(74) *Attorney, Agent, or Firm* — Buchanan Ingersoll & Rooney PC (57) ABSTRACT

A stent includes a plurality of wavy annular bodies each formed in an annular shape from a wavy linear member, and a connection part provided between the adjacent wavy annular bodies, interconnecting the adjacent wavy annular bodies coaxially, weaker than the wavy annular bodies and rupturable. The connection part extends in a slanting manner relative to an axial direction in which the wavy annular bodies are aligned, and interconnects that one inflexed part of one wavy annular body which is curved in a shape projected toward the other wavy annular body adjacent to the one wavy annular body and that the other inflexed part of the other wavy annular body which is curved in a shape projected toward the one wavy annular body.

9 Claims, 10 Drawing Sheets

STENT

TECHNOLOGICAL FIELD

The present invention relates to a stent to be indwelled in a stenosed or occluded lesion in a lumen in vivo to maintain patency of the lumen.

BACKGROUND DISCUSSION

Stents are medical devices used for improving a stenosed or occluded lesion generated in a lumen in vivo, such as a blood vessel, bile duct, trachea, esophagus, urethra, etc. In general, a stent has a configuration in which a plurality of wavy annular bodies each formed in an annular shape from a wavy linear member are coaxially aligned and interconnected to obtain a network-like tubular body.

For instance, Japanese Patent Laid-open No. 2000-316983 describes a stent which has connection parts weaker than wavy annular bodies and which is formed in an overall tubular shape by interconnecting the adjacent wavy annular bodies by the connection parts. Even in the case where the stent is indwelled in a bifurcated blood vessel, after the stent is indwelled (i.e., placed in the blood vessel), a balloon catheter positioned inside the stent may pass through an opening in the network of the stent so that a portion of the balloon passes to the outside of the stent from the inside of the stent, and when the balloon is inflated, a connection part may rupture. This then requires an operation for putting a further stent indwelling in a branch blood vessel bifurcated from the bifurcated blood vessel.

Intensive and extensive investigations by the inventors here about the rupture of the connection part in the above-mentioned stent led to the discovery that only an extremely small part of the force exerted on the stent from the balloon acts on the connection part.

Specifically, in the process of rupturing the connection part, the balloon comes into contact with the wavy linear member while being inflated, and that part of the wavy linear member which extends slantly relative to the axial direction of the stent between a mountain crest portion and a valley bottom portion of the wavy linear member is pulled in a direction along the part. Therefore, the force exerted on the stent from the balloon acts on the connection part, mainly in a slanting manner relative to the axial direction of the stent (hereinafter, the direction that is slanted relative to the axial direction in which the force from the balloon acts mainly is referred to as the "main stress direction"). On the other hand, in the above-mentioned stent, the connection parts are formed parallel to the axial direction of the stent. Therefore, there is little possibility that the main stress direction and the direction of the connection part coincide with each other. This is why only an extremely small part of the force exerted on the stent from the balloon acts on the connection part in the known stent described above.

To permit easier rupture of the connection part, the connection parts may be formed to be weaker than necessary, which may lead to rupture of the connection parts at times other than at the time of balloon inflation. Or, in order to prevent the rupture of the connection parts from occurring at time other than the time of balloon inflation, the connection parts may be formed to have an enhanced rupture strength, which may make it difficult to rupture the connection part at the time of balloon inflation; in this case, there is a risk that an excessive expansive force may be exerted from the balloon.

SUMMARY

The disclosed stent makes it possible to avoid weakening of the connection part more than necessary, so that strength of the connection part can be secured, while also reducing the expansive force of the balloon required to rupture the connection part.

According to one aspect of the disclosure here, a stent includes a plurality of wavy annular bodies each formed in an annular shape from a wavy linear member; and connection parts between the adjacent wavy annular bodies. The connection parts interconnect the adjacent wavy annular bodies coaxially, are weaker than the wavy annular bodies and are configured to be ruptured. Each of the connection part extends in a slanting manner relative to an axial direction in which the wavy annular bodies are aligned, and interconnects that one inflexed part of one wavy annular body which is curved in a shape projecting toward the other wavy annular body adjacent to the one wavy annular body and that the other inflexed part of the other wavy annular body which is curved in a shape projecting toward the one wavy annular body.

In the stent configured as above, the connection part extends in a slanting manner relative to the axial direction, and interconnects the one inflexed part and the other inflexed part. This helps ensure that when the balloon is inflated for rupturing the connection part, there is little difference between the main stress direction and the direction of the connection part, so that the force exerted on the stent from the balloon is rather easily exerted on the connection part. Consequently, it is possible to avoid weakening the connection part more than necessary, so that strength of the connection part can be secured, and, simultaneously, the expansive force of the balloon required for rupture of the connection part can be suppressed.

In addition, a configuration may be adopted in which the one inflexed part has an inner edge portion curved in a shape projected toward the other wavy annular body, the other inflexed part has an inner edge portion curved in a shape projected toward the one wavy annular body, and the connection part extends in parallel to a tangential line interconnecting the inner edge portion of the one inflexed part and the inner edge portion of the other inflexed part. In this case, the main stress direction and the direction of the connection part are substantially coincident with each other, so that a greater force can easily act on the connection part. As a result, the need to weaken the connection part is further reduced, so that strength of the connection part can be secured, and, simultaneously, the expansive force of the balloon required for rupture of the connection part can be further suppressed.

Another configuration may be adopted in which the one inflexed part has an inner edge portion curved in a shape projected toward the other wavy annular body, the other inflexed part has an inner edge portion curved in a shape projected toward the one wavy annular body, and the connection part is located at a position deviated from a position on a tangential line interconnecting the inner edge portion of the one inflexed part and the inner edge portion of the other inflexed part. This helps ensure that, when the balloon is inflated for rupture of the connection part, the connection part is liable to be twisted, so that a bending moment is generated in the connection part in addition to a tensile stress, which promises easier rupture of the connection part. Accordingly, the need to weaken the connection part is further reduced, so that strength of the connection part can be secured, and, simultaneously, the expansive force of the balloon required for rupture of the connection part can be further suppressed.

The connection part may have a width smaller than the width of the linear members. In this case, the connection part is weaker, as compared with the wavy annular bodies, so that rupture at the connection part becomes more liable to occur. Consequently, an opening can be formed in the side surface of the stent, while maintaining the strength of the wavy annular bodies for maintaining patency of a lumen.

The connection part may be provided with at least one of a cut, a notch, and a hole. In this case, also, the connection part is weakened, as compared with the wavy annular bodies, so that rupture at the connection part is permitted to occur more easily. Accordingly, an opening can be formed in the side surface of the stent, while maintaining the strength of the wavy annular bodies for maintaining patency of a lumen.

In addition, crystal grains in the connection part may be set greater than crystal grains in the wavy annular bodies. With such a setting, also, the connection part is weakened, as compared with the wavy annular bodies, so that rupture at the connection part is more liable to occur. Consequently, an opening can be formed in the side surface of the stent, while maintaining the strength of the wavy annular bodies for maintaining patency of a lumen.

Another aspect of the disclosure here involves a stent comprised of: a plurality of wavy annular bodies coaxially arranged in an axial direction so that adjacent wavy annular bodies are positioned axially adjacent one another; wherein each wavy annular body includes a plurality of circumferentially adjacent strut portions and a plurality of curved inflexed portions each connecting two of the strut portions which are circumferentially adjacent one another; and wherein the curved inflexed portions of each wavy annular body include crest-shaped curved inflexed portions and trough-shaped curved inflexed portions which are curved in opposite directions. A plurality of axially adjacent pairs of wavy annular bodies are connected to each other by connection parts, each of the connection parts being weaker than the wavy annular bodies to allow the connection parts to rupture in advance of the axially adjacent wavy annular bodies when a radially outwardly directed force is applied to the stent from inside the stent. Each connection part has one end directly connected to a crest-shaped curved inflexed portion of one of the wavy annular bodies and an opposite end directly connected to a trough-shaped curved inflexed portion of the axially adjacent wavy annular body, and each connection part extends in a slanting manner relative to the axial direction.

According to another aspect, a method of using a stent involves positioning a stent in a lumen in vivo, wherein the stent includes: a plurality of wavy annular bodies coaxially arranged in an axial direction and each including a plurality of curved inflexed parts at each axial end of the wavy annular body; and a plurality of connecting parts each connecting one of the curved inflexed parts of one wavy annular body which curves to project toward an other wavy annular body positioned axially adjacent the one wavy annular body and an other inflexed part of the other wavy annular body which curves to project toward the one wavy annular body; and each connection part extending in a slanting manner relative to the axial direction; each wavy annular body also comprising void parts. The method also involves positioning a balloon catheter inside the stent so that an inflatable balloon forming a part of the balloon catheter is in the stent, moving the balloon catheter to position the balloon in one of the void parts of one of the wavy annular bodies, inflating the balloon while the balloon is positioned in the one void part, and continuing to inflate the balloon part until one of the connection parts ruptures and before any part of the wavy annular bodies ruptures, the one connection part being located adjacent the one void part.

DETAILED DESCRIPTION

Set forth below is a detailed description of embodiments of the stent disclosed here. In the embodiments described below, common features in the different embodiments which exhibit similar functions are identified by similar reference numbers, and a detailed description of such common features is not repeated in the description of subsequent embodiments. To facilitate an understanding of the disclosure here, the ratios of dimensions in the drawings are exaggerated and, therefore, may be different from the actual ratios.

Figure 1:
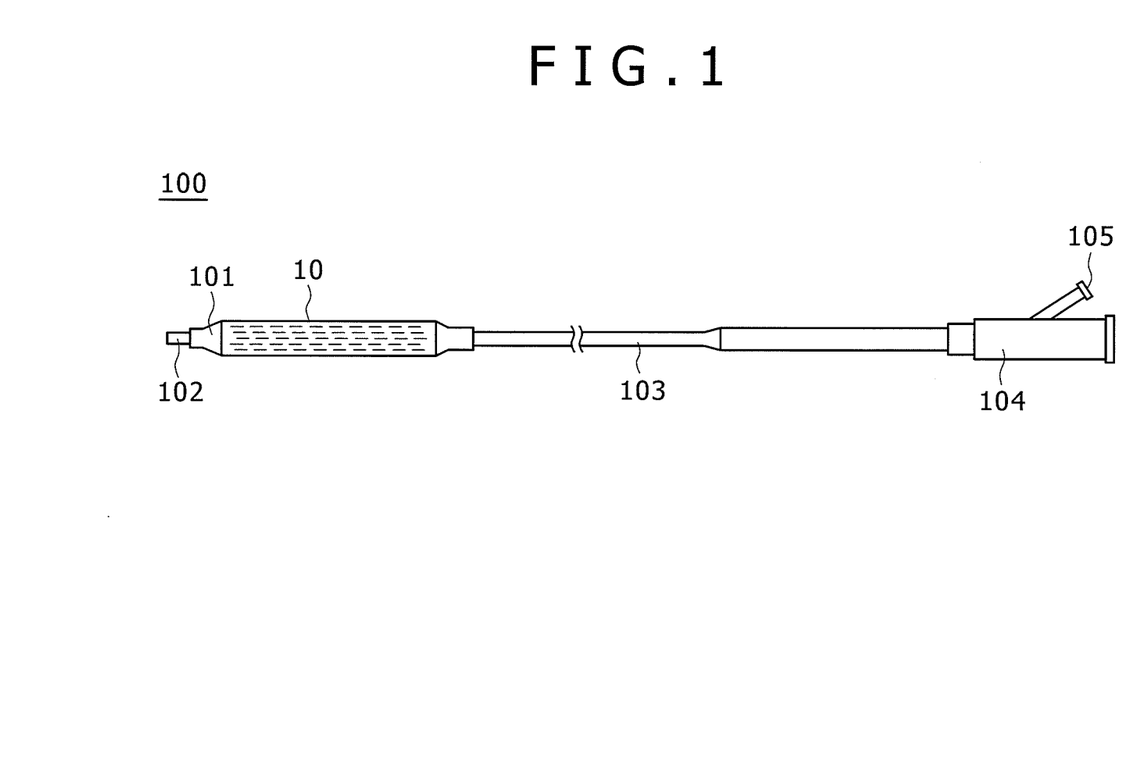
FIG. 1 is a schematic view showing the configuration of a balloon catheter for indwelling a stent.

Referring to FIG. 1, a stent 10 according to a first embodiment disclosed here is a balloon-expandable stent. Specifically, the stent 10 is indwelled in a lumen such as a blood vessel by a balloon catheter 100 for expanding the stent 10.

The balloon catheter 100 has a flexible outer tube 103 through which an actuating fluid can be fed, a balloon 101 at the distal end of the outer tube 103 and which can be inflated and deflated by injecting and discharging the actuating fluid, and the stent 10 mounted so as to cover the balloon 101. In addition, the balloon catheter 100 has an inner tube 102 which concentrically passes through the inside of the outer tube 103, and a branch hub 104 provided at the proximal end of the outer tube 103. The branch hub 104 is provided with an injection port 105 through which the actuating fluid is injected and discharged. The injection port 105 communicates with a lumen (not shown) formed between the inner tube 102 and the outer tube 103, and communicates with the balloon 101 through the lumen. The balloon catheter 100 may be of a rapid exchange type in which a guide wire is passed through only a catheter portion ranging from an intermediate position to the distal end, or may be of an over-the-wire type in which a guide wire is passed through a catheter portion ranging from the proximal end to the distal end.

Figure 2:
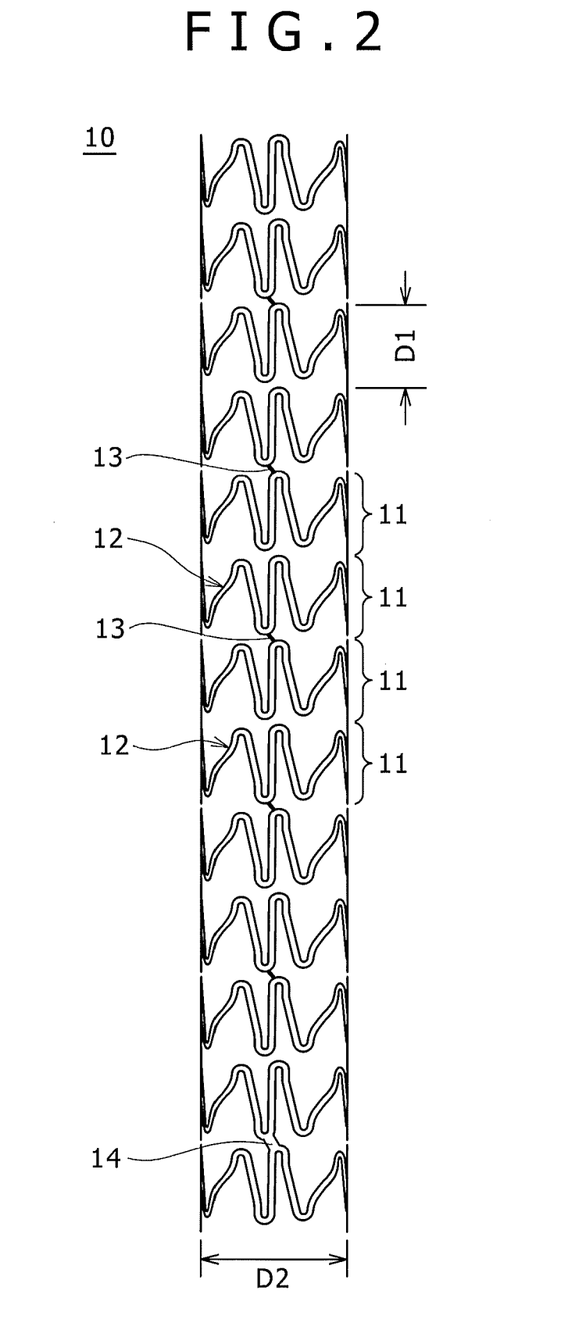
FIG. 2 is a side view of a stent according to a first embodiment before expansion.
Figure 3:
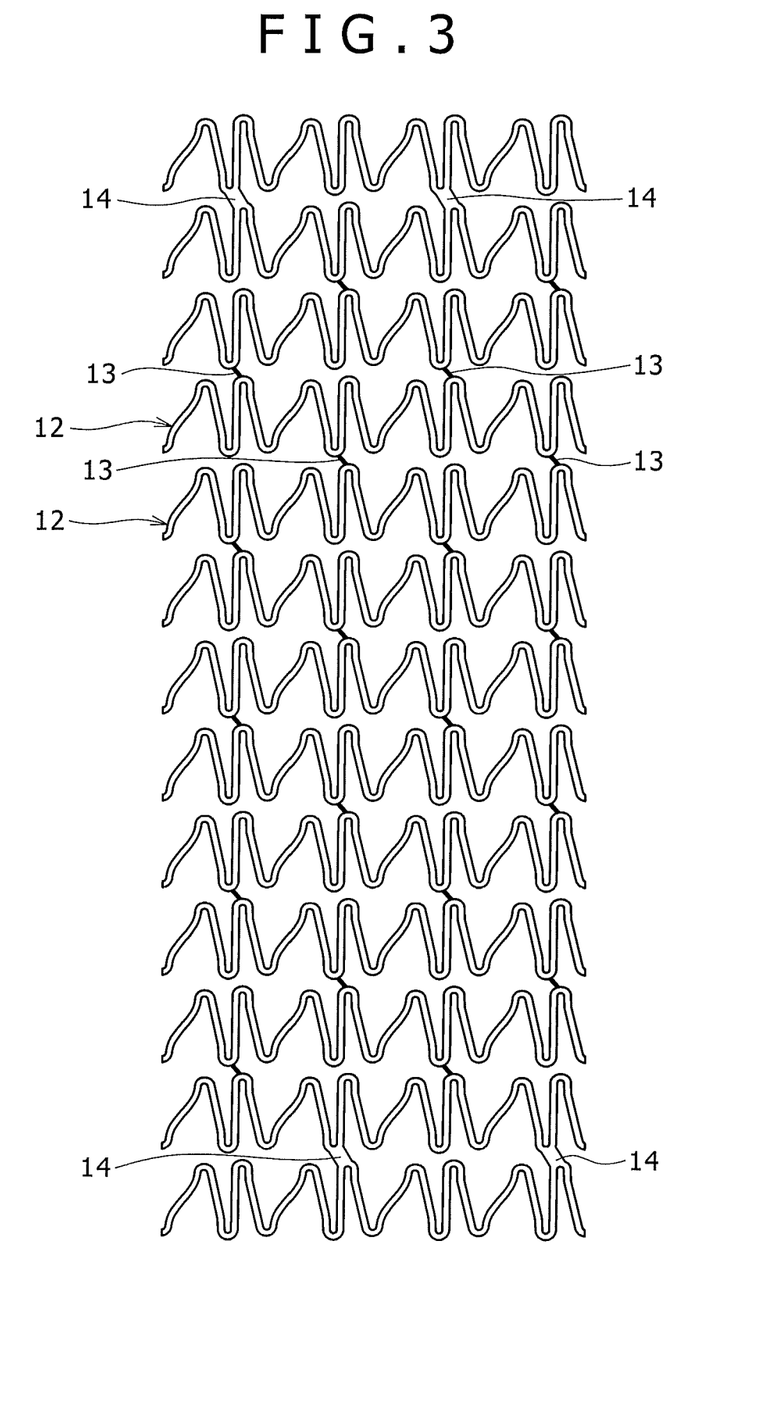
FIG. 3 is a developmental view of the stent according to the first embodiment.

As shown in FIGS. 2 and 3, the stent 10 includes a plurality of wavy annular bodies 11 each possessing an annular shape comprised of a wavy strut 12 (continuous wavy linear member), and connection parts 13 provided between adjacent wavy annular bodies 11. The connection parts each interconnect the adjacent wavy annular bodies 11 coaxially, are weaker than the wavy annular bodies 11 and are configured to be ruptured (i.e., are rupturable). The wavy annular bodies 11 and the connection parts 13 are formed integrally in one piece as a single unit, and the stent 10 as a whole is so to speak a network-like tubular body. In the illustrated embodiment of the stent, the axially adjacent wavy annular bodies 11 do not axially overlap one another. That is, with reference to FIG. 2, and assuming the top end of the stent is referred to as the distal end and the bottom end is referred to as the proximal end, the distal-most portion of each wavy annular bodies 11 does not axially overlap the proximal-most portion of the wavy annular body 11 that is axially adjacent in the distal direction, and the proximal-most portion of each wavy annular body 11 does not axially overlap the distal-most portion of the wavy annular body 11 that is axially adjacent in the proximal direction.

The stent 10 includes two connection parts 13 disposed between and connecting each pair of axially adjacent wavy annular bodies 11. The two connection parts 13 connecting each pair of axially adjacent wavy annular bodies 11 are spaced apart along the circumferential direction of the wavy annular bodies 11. The two connection parts 13 connecting each pair of axially adjacent wavy annular bodies 11 are provided at positions in the circumferential direction of the wavy annular bodies 11 which are substantially opposite to each other (diametrically opposite positions). In addition, one pair of the connection parts 13 and the other pair of the connection parts 13 adjacent to the one pair of the connection parts 13 in an axial direction in which the wavy annular bodies 11 are aligned (this direction will hereinafter be referred to simply as the axial direction) are shifted from each other by about 90° in the circumferential direction of the wavy annular bodies 11. That is, except for the wavy annular body 11 at each end of the stent, the one of the two connection parts 13 connecting each pair of axially adjacent wavy annular bodies 11 is circumferentially shifted by about 90° relative to one of the two connection parts 13 connecting the next successive pair of axially adjacent wavy annular bodies 11, and the other of the two connection parts 13 connecting each pair of axially adjacent wavy annular bodies 11 is circumferentially shifted by about 90° relative to the other of the two connection parts 13 connecting the next successive pair of axially adjacent wavy annular bodies 11. Stated differently, considering any three axially adjacent wavy annular bodies 11 of the stent (exclusive of the wavy annular body 11 at each end of the stent) in which a second wavy annular body is positioned axially between axially adjacent first and third wavy annular bodies, one of the connection parts 13 connecting the first and second wavy annular bodies 11 is circumferentially shifted by about 90° relative to one of the connection parts 13 connecting the second and third wavy annular bodies 11, and the other connection part 13 connecting the first and second adjacent wavy annular bodies 11 is circumferentially shifted by about 90° relative to the other connection part 13 connecting the second and third wavy annular bodies 11. The connection part 14 provided at each end of the stent in the axial direction of the stent 10 are not configured for rupture, and are formed to possess a greater width than the other connection parts 13. The connection part 14 at each axial end of the stent provides reinforcement. The connection parts 13 constitute first connection parts and the connection parts 14 constitute second connection parts different from the first connection parts 13.

By way of example, the length D1 of each wavy annular body 11 in the axial direction is about 0.5 to 2.0 mm, preferably 0.9 to 1.5 mm, and the diameter D2 of each wavy annular body 11 in a non-expanded state is about 0.8 to 2.5 mm, preferably 0.9 to 2.0 mm.

The material forming the wavy annular bodies 11 and the connection parts 13 is preferably a bio-compatible material, for example stainless steel, tantalum or tantalum alloy, platinum or platinum alloy, gold or gold alloy, cobalt-based alloy, cobalt-chromium alloy, titanium alloy, niobium alloy or the like. Of various stainless steels, preferred is SUS316L, which is the highest of the stainless steels in corrosion resistance.

The wavy annular bodies 11 and the connection parts 13 are preferably formed in a predetermined pattern, starting with a tubular member or pipe (specifically, a metallic pipe) and then removing portions other than the struts 12 and the connection parts 13 from the tubular member/pipe. For instance, the wavy annular bodies 11 and the connection parts 13 can be formed by removing the unnecessary portions from a metallic pipe by an etching method using chemicals and masking called photofabrication, an electric discharge machining method using a die, a cutting method (for example, mechanical polishing, a laser beam cutting) or the like. After such a forming process, edges of the struts 12 are removed by chemical polishing or electrolytic polishing, to obtain smooth finished surfaces.

Further, annealing may be conducted, after being formed into the predetermined pattern. As a result of the annealing, flexibility and plasticity of the stent 10 as a whole are enhanced, good indwelling performance of the stent 10 in a bent blood vessel is achieved, physical stimuli given to the inside walls of blood vessels by the stent 10 are reduced, and the possibility of causing restenosis can be lowered. For preventing formation of an oxide film on the surfaces of the stent 10, the annealing is preferably carried out by heating to a temperature of 900 to 1200° C. in an inert gas atmosphere (for example, in a mixed gas of nitrogen and hydrogen), and subsequent slow cooling.

Figure 4:
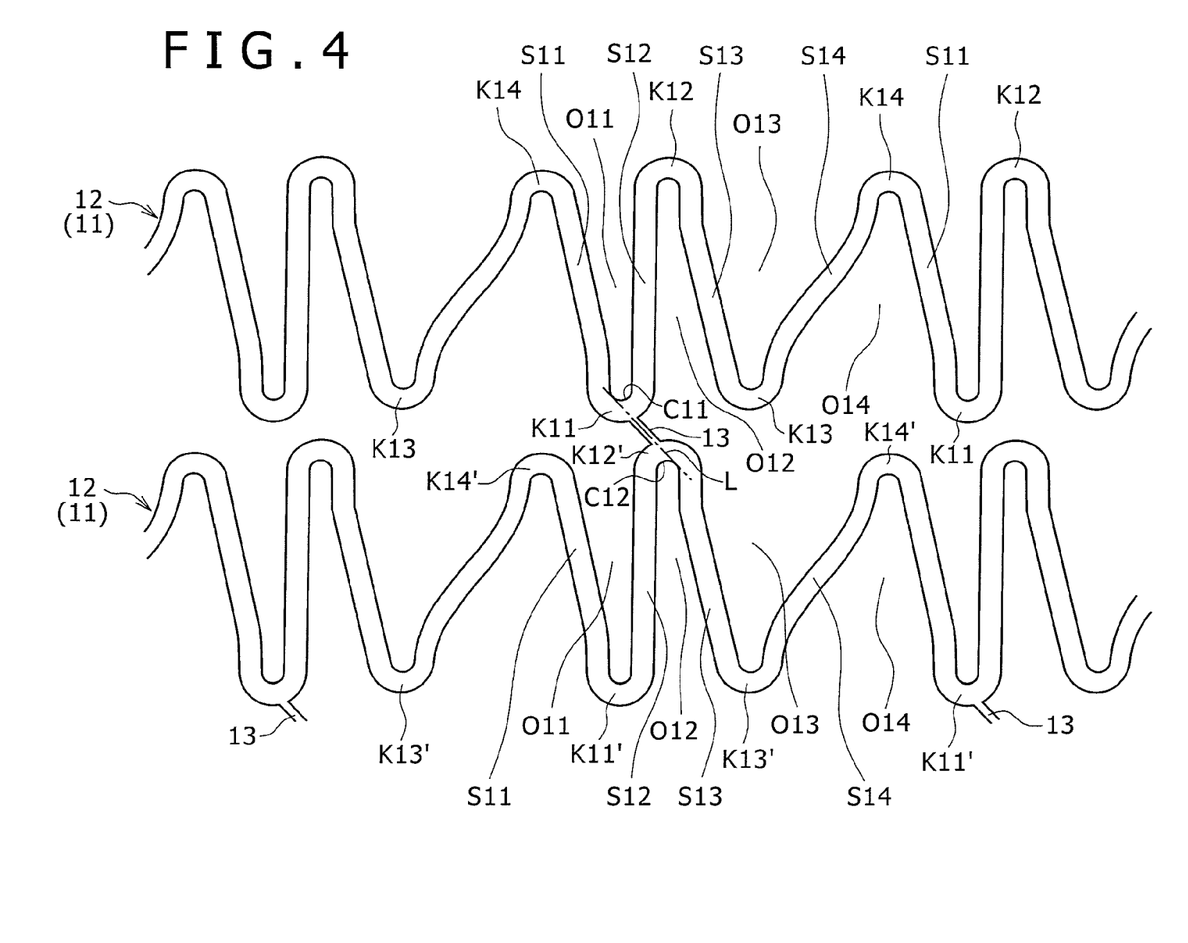
FIG. 4 is a partial enlarged view showing, in an enlarged form, a connection part of the stent according to the first embodiment and the vicinity of the connection part.

As shown in FIG. 4, the wavy annular body 11 (the strut 12) each have inflexed (inflection) parts K11 (K11'), K12 (K12'), K13 (K13'), K14 (K14') which constitute mountain (crest) portions and valley (bottom or trough) portions of the wavy shape, and strut portions S11, S12, S13, S14 which interconnect the inflexed parts in succession. In this illustrated embodiment, the strut portions S11, S13 and S14 are slant parts which extend in a slanting manner relative to the axial direction. The circumferentially adjacent strut portions are connected by one of the inflexed parts. The inflexed parts K11 (K11'), K12 (K12'), K13 (K13'), K14 (K14') are each curved in a gently circular, arcuate or arc-shaped form such as the substantially U-shaped form shown in FIG. 4.

A void part O11 formed between the strut portion S11 and the strut portion S12, and a void part O12 formed between the strut portion S12 and the strut portion S13 are substantially equal in size (i.e., substantially equal in area). In addition, a void part O13 formed between the strut portion S13 and the strut portion S14, and a void part O14 formed between the strut portion S14 and the strut portion S11 are substantially equal in size (i.e., substantially equal in area). The void parts O13, O14 are greater in size (i.e., greater in area) than the void parts O11, O12.

The connection part 13 extends in a slanting manner relative to the axial direction, and interconnects an inflexed part K11 (one inflexed part) of one wavy annular body 11 which is curved in a shape projected toward the axially adjacent wavy annular body 11 (the other wavy annular body) and an inflexed part K12' (the other inflexed part) of the axially adjacent wavy annular body 11 which is curved in a shape projected toward the one wavy annular body 11. In other words, the connection part 13 does not interconnect inflexed parts projecting in the same direction (for example, K11 and K11', or K12 and K12') or inflexed parts projecting in spacing-apart directions (for example, K12 and K13', or K13' and K14) of the adjacent wavy annular bodies 11, but interconnects the inflexed parts K11 and K12' of the adjacent wavy annular bodies 11 which project toward each other.

The inflexed part K11 has an inner edge portion C11 curved in a shape projected toward the other wavy annular body 11. Similarly, the inflexed part K12' has an inner edge portion C12 in a shape projected toward the one wavy annular body 11. The connection part 13 (the centerline of the connection part 13) extends on a line L that is a tangent to both the inner edge portion C11 and the inner edge portion C12. The tangential line L thus interconnects the inner edge portion C11 and the inner edge portion C12. The inner edge portion C11 and the inner edge portion C12 connected by the tangential line L is curved in shape. That is, the tangential line L is connected to or intersects the inner edge portion C11 and the inner edge portion C12 at a curved portion.

In addition, the connection parts 13 possess a smaller width than the struts 12. The width of the strut 12 is for example about 0.09 to 0.15 mm, and the width of the connection part 13 is for example about 0.01 to 0.05 mm. The material thickness of the struts 12 and the connection parts 13 is for example about 0.05 to 0.12 mm. The cross-sectional area of the connection part 13 is for example about 1/50 to 1/2, preferably about 1/20 to 1/10, of the cross-sectional area of the strut 12.

The placement of the stent 10 indwelling in a bifurcated blood vessel and rupture of the connection parts 13 is as follows.

The stent 10 is indwelled in a bifurcated blood vessel by use of the balloon catheter 100. To do this, a guide wire is inserted in the inner tube 102 which is open at its distal end, and the balloon 101 and the stent 10 are introduced to the bifurcated blood vessel by using the guide wire as a guide. Thereafter, the actuating fluid is injected via the injection port 105, to flow into the balloon 101, whereby the balloon 101 is inflated.

Figure 5A:
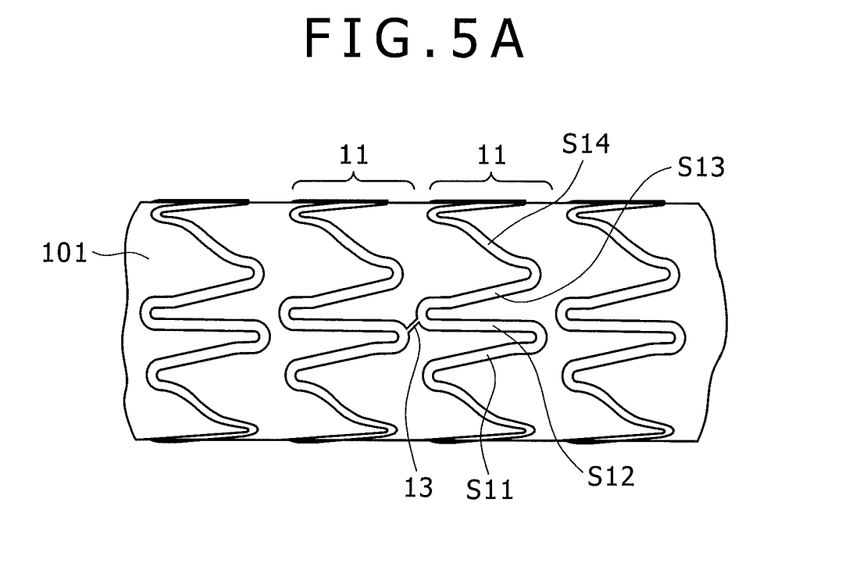
FIG. 5A is a partial enlarged side view of the stent before inflation of a balloon.
Figure 5B:
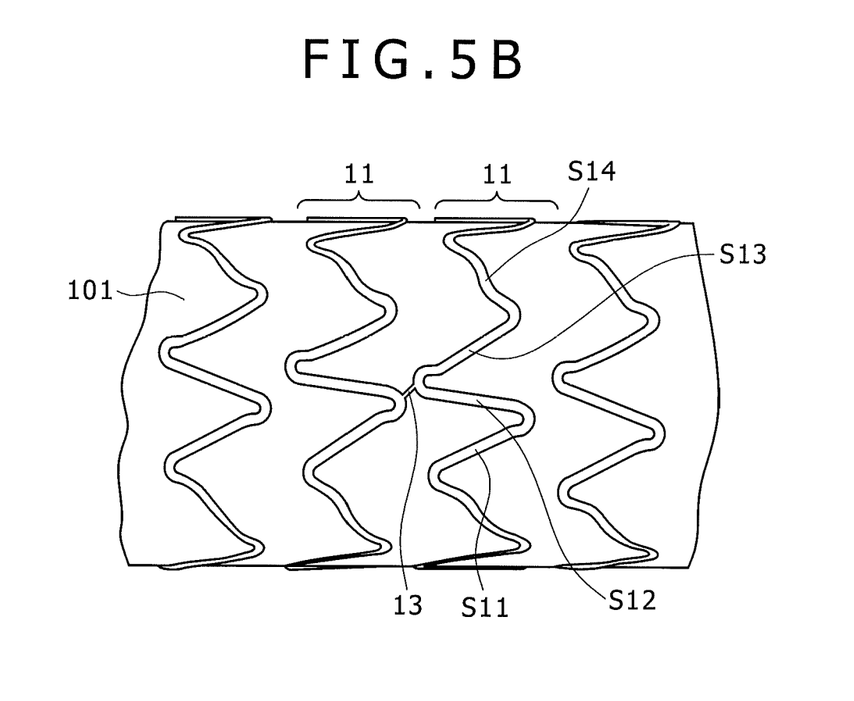
FIG. 5B is a partial enlarged side view of the stent after inflation of the balloon.

As a result, as shown in FIG. 5A to FIG. 5B, the wavy annular bodies 11 are expanded radially outwardly from the inside, and are plastically deformed in the manner of being stretched radially, whereby the stent 10 is indwelled in the blood vessel in an expanded state. In this case, the strut portions S11, S12, S13, S14 are mutually spaced farther than before the expansion of the stent 10 (i.e., the distance between the circumferentially adjacent slanting members increases), so that the wavy annular bodies 11 (the stent 10) are set into an opened state in which the void parts O11, O12, O13, O14 are widespread. The diameter of the wavy annular body 11 upon expansion is, for example, about 2 to 6 mm.

Figure 6:
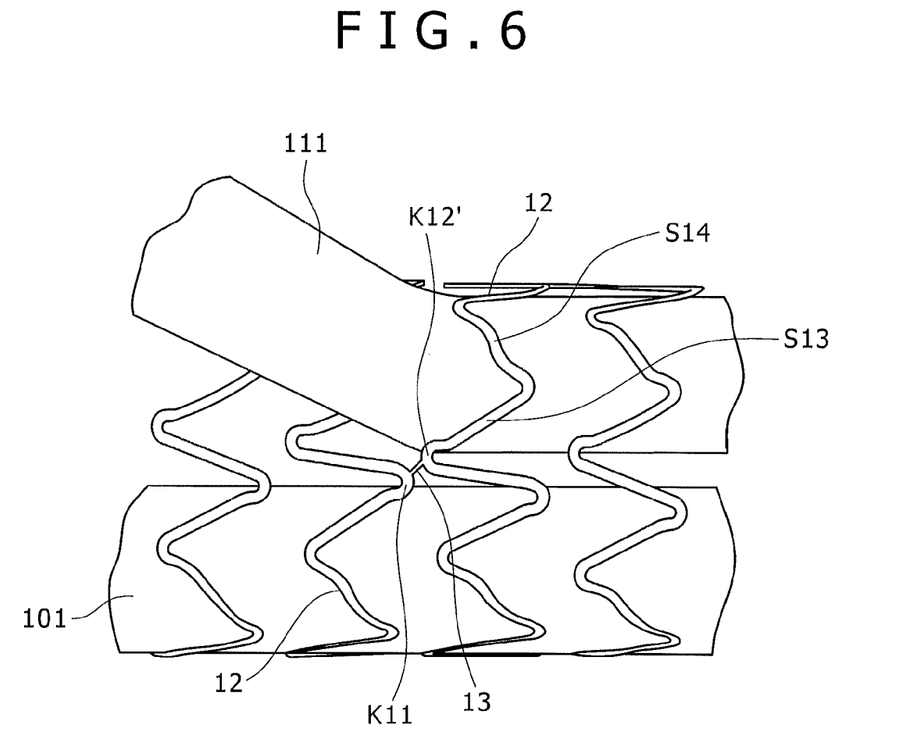
FIG. 6 is a partial enlarged perspective view showing the condition where a balloon is passed through a void part in a side surface of the stent.

Thereafter, to rupture the connection parts 13, the actuating fluid is discharged via the injection port 105, whereby the balloon 101 is once deflated, producing a gap between the stent 10 and the balloon 101. Then, as shown in FIG. 6, in the same manner as the balloon catheter 100 is introduced, another balloon catheter is introduced into the blood vessel. The balloon 111 of the other balloon catheter is positioned in the gap between the balloon 101 and the stent 10, and is passed through the void part O13 between the strut portion S13 and the strut portion S14. Since the size or area of the void part O13 is greater than the size or area of the void parts O11 and O12, the balloon 111 can pass through the void part O13 rather easily. The distal end of the balloon 111 thus passing through the void part O13 enters into a branch blood vessel bifurcated from a main blood vessel in which the stent 10 is indwelled.

Figure 7:
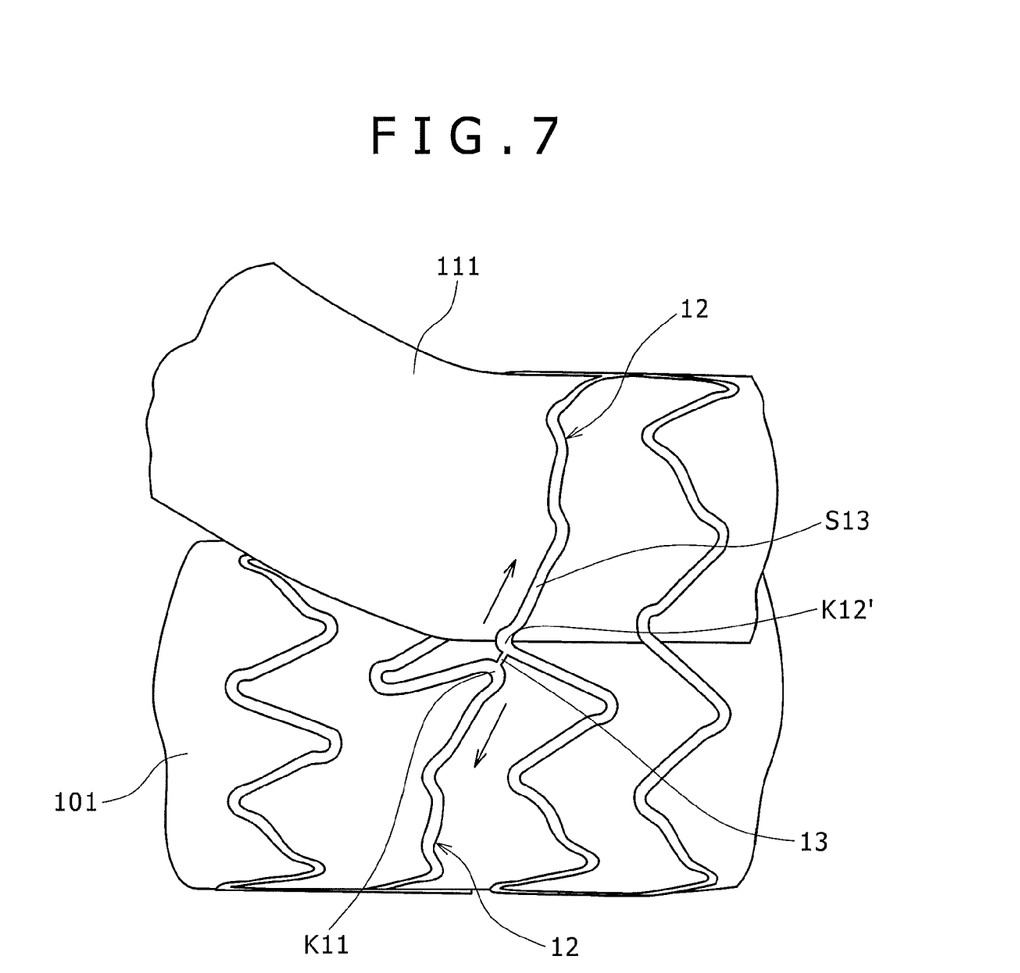
FIG. 7 is a partial enlarged perspective view showing the condition where the balloon passed through the void part is inflated.

Thereafter, as shown in FIG. 7, the actuating fluid is injected into the balloon 101 and the balloon 111 to thereby inflate the balloons. The balloon 101 thus inflated presses the stent 10 against the vessel wall of the main blood vessel to hold the stent 10, thereby inhibiting or preventing the position of the stent 10 from being shifted due to the inflation of the balloon 111. On the other hand, the balloon 111 while being inflated expands the wavy annular bodies 11 radially outward from the inside.

Due to the inflation of the balloon 111, a force is exerted along the strut portion S13. In addition, since the connection part 13 interconnects the inflexed part K11 and the inflexed part K12', one end of the connection part 13 is pulled by the strut 12 (the other wavy annular body 11) making contact with the balloon 111, whereas the other end of the connection part 13 is held by another strut 12 (the one wavy annular body 11) pressed by the balloon 101.

Then, when the pressure inside the balloon 111 reaches a sufficient level (predetermined pressure), the connection part 13 is ruptured and an opening is formed in the side surface of the stent 10. For example, at the time of expansion of the wavy annular bodies 11, a pressure of about 9 atm is exerted on the balloon 111, and, at the time of rupture of the connection part 13, the pressure inside the balloon 111 reaches about 13 atm.

In the stent 10 disclosed here, the connection part 13 extends in a slanting manner relative to the axial direction, and interconnects the inflexed part K11 and the inflexed part K12'. When the balloon 111 is inflated, therefore, there is little difference between the main stress direction along the strut portion S13 and the direction of the connection part 13, so that the expansive force of the balloon 111 is easily exerted on the connection part 13. Accordingly, it is possible to avoid weakening the connection part 13 more than necessary, so that the strength of the connection part 13 can be secured, and, simultaneously, the expansive force of the balloon 111 required for rupture of the connection part 13 can be suppressed.

In addition, because the connection part 13 is parallel to the tangential line L, the main stress direction and the direction of the connection part are substantially coincident. This helps ensure that a greater force acts on the connection part 13, the need to weaken the connection part 13 is further reduced, so that strength of the connection part 13 can be secured, and, simultaneously, the expansive force of the balloon 111 required for rupture of the connection part 13 can be further suppressed.

As mentioned, the connection part 13 is smaller than the struts 12 in width and is weaker than the wavy annular bodies 11. Rupture at the connection part 13 thus occurs more easily upon inflation of the balloon 111. Accordingly, an opening can be formed in the side surface of the stent 10 while maintaining the strength of the wavy annular bodies 11 for maintaining patency of the blood vessel.

In addition, with the opening thus formed in the side surface of the stent 10, the bloodstream flowing from the main blood vessel into the branch blood vessel is restrained from being hampered, whereby generation of thrombus at the bifurcated blood vessel can be prevented from occurring. Further, it is made possible to insert a balloon catheter or a stent delivery system into the branch blood vessel and, hence, to put a stent 10 indwelling in the branch blood vessel by way of the opening formed in the side surface of the stent 10.

Figure 8:
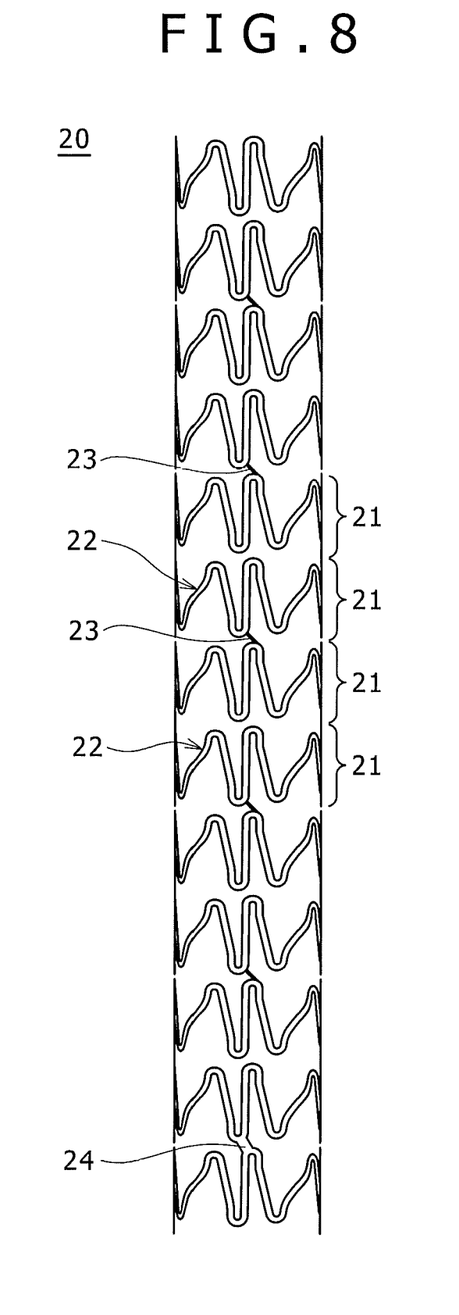
FIG. 8 is a side view of a stent according to a second embodiment, before expansion.
Figure 9:
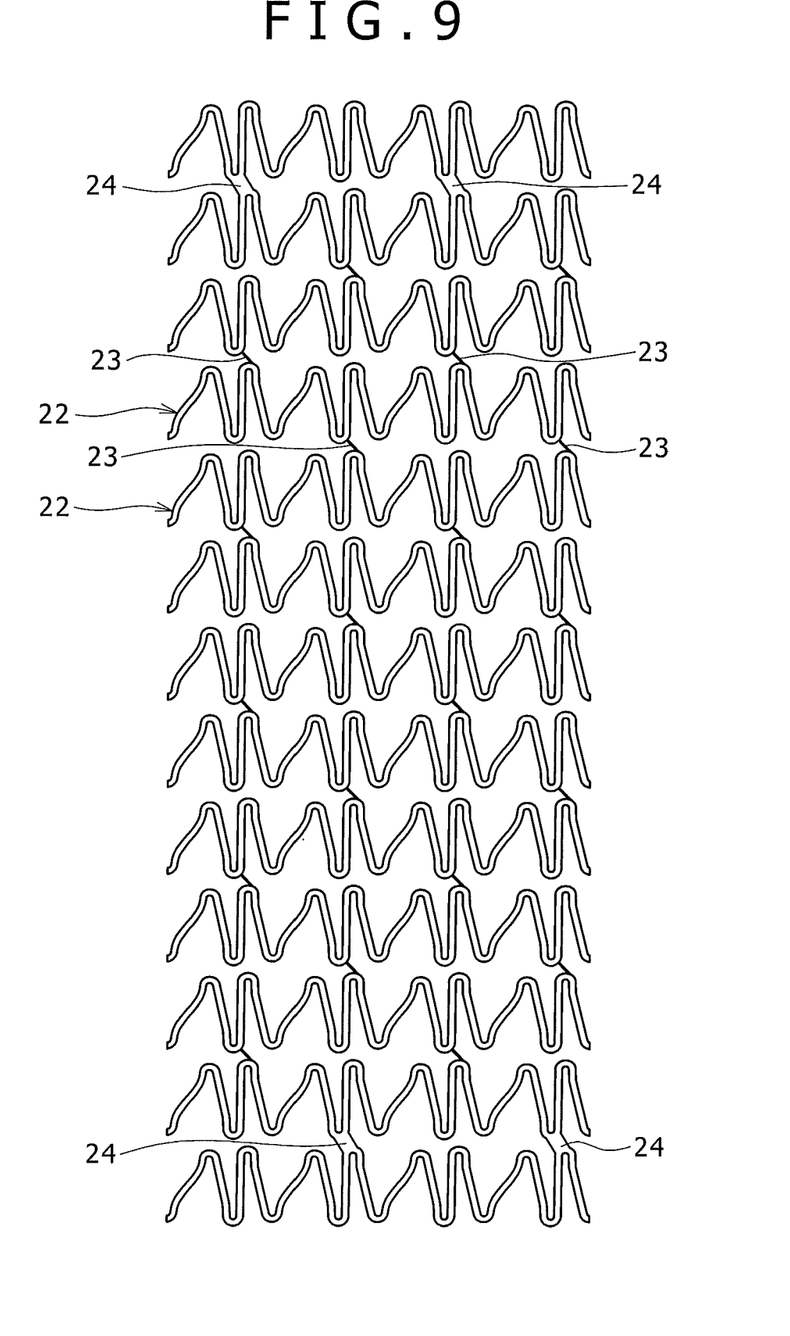
FIG. 9 is a development view of the stent according to the second embodiment.
Figure 10:
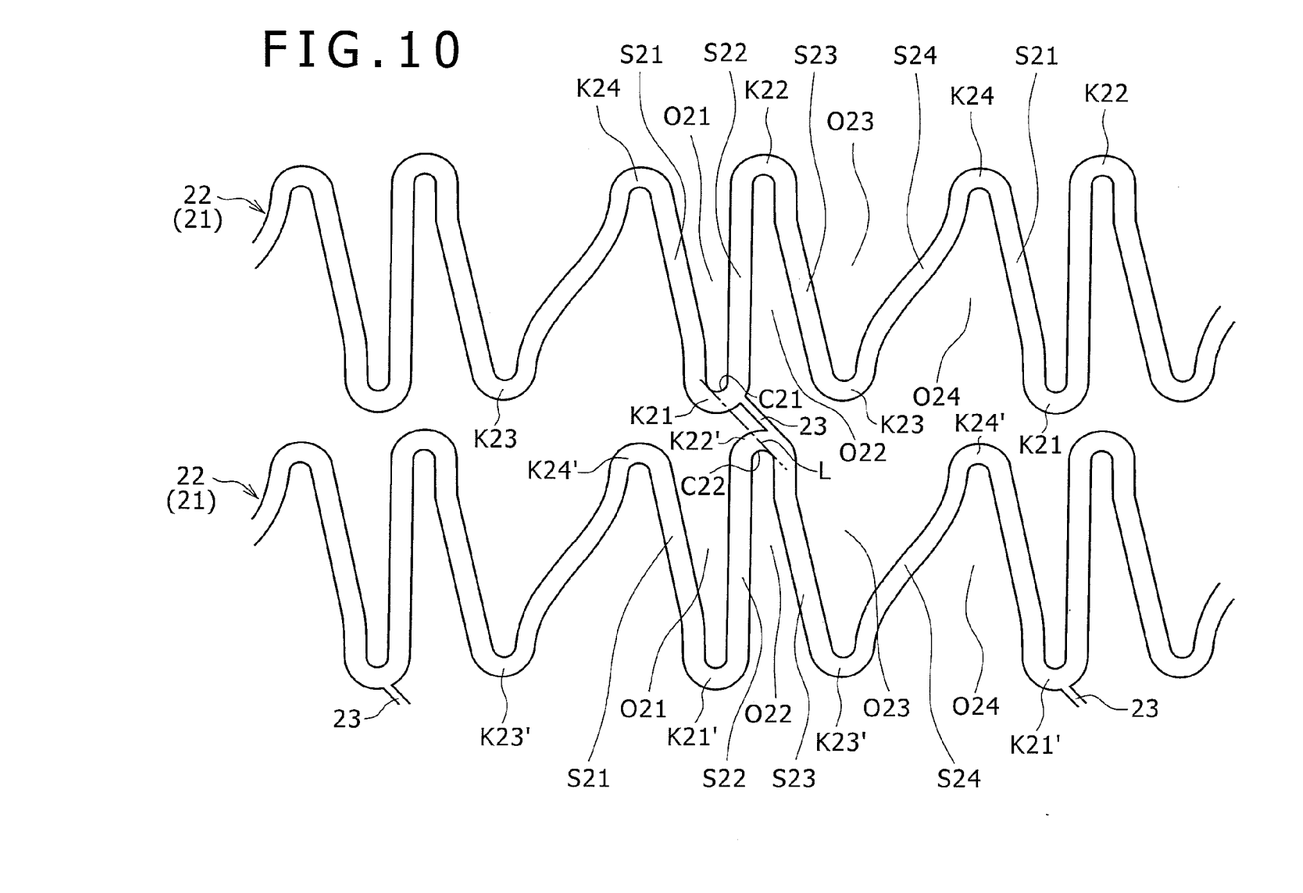
FIG. 10 is a partial enlarged view showing, in an enlarged form, a connection part of the stent according to the second embodiment and the vicinity of the connection part.

FIGS. 8-10 illustrate a stent 20 according to a second embodiment. This embodiment of the stent is substantially the same as the stent 10 according to the first embodiment, but differs from the first embodiment of the stent in the configuration of a connection part 23. The connection part 23 is parallel to the tangential line L in a manner similar to the connection part 13. However, unlike the connection part 13, the connection part 23 doesn't extend on the tangential line L. That is, the connection part 23 is spaced from the tangential line L.

With the connection part 23 thus located at a position deviated from the tangential line L, the connection part 23 is liable to be twisted when the balloon 111 is inflated after the stent 20 is indwelled in a blood vessel. In this instance, a bending moment is generated in the connection part 23 in addition to a tensile stress, leading to an easier rupture of the connection part 23. Accordingly, the need to weaken the connection part 23 is more reduced, so that the strength of the connection part 23 can be secured, and, simultaneously, the expansive force of the balloon 111 required for the rupture of the connection part 23 can be further suppressed. The effects associated with this second embodiment of the stent 20, including the arrangement and configuration of the connection part 23, is the same as the stent 10 described above.

The invention here is not limited to the above-described embodiments, and the associated features and details. For example, the connection part may not necessarily be parallel to the tangential line L which is tangent to the above-mentioned inner edge portions, insofar as the connection part extends in a slanting manner relative to the axial direction. In addition, it suffices for the connection part to interconnect inflexed parts which project toward each other of the adjacent wavy annular bodies. Thus, it is possible for the inflexed part K13 and the inflexed part K14' in the above-described embodiments to be interconnected by the connection part.

In addition, the shape of each of the inflexed parts and the inner edge portions is not limited to the curved shape; for example, the shape may be a bent shape like the shape of the bottom of a V-shaped form. In this case, the tangential line L interconnects the vertex of one bent inner edge portion and the vertex of the other bent inner edge portion.

The connection parts are required only to be weaker than the wavy annular bodies and be capable of being ruptured. The connection parts are not limited to those smaller than the wavy linear members in width as in the above-described embodiments. For example, the connection parts may each be a part which is substantially equal to the wavy linear member in width and which is provided with at least one of a cut, a notch, and a hole. In this case, also, the connection parts are weaker than the wavy annular bodies, which facilitates easier rupture at the connection part, and makes it possible to form an opening in the side surface of the stent while maintaining the strength of the wavy annular bodies for maintaining patency of a lumen. As another possibility, a configuration may be adopted in which crystal grains in the connection parts are greater than crystal grains in the wavy annular bodies, whereby the connection parts are made weaker than the wavy annular bodies. In this case, also, like in the above-mentioned configurations, easier rupture at the connection part is possible, and an opening can be formed in the side surface of the stent while maintaining the strength of the wavy annular bodies for maintaining patency of a lumen. The reference to crystal grains is a reference to the diameter or size of the crystal grains of material forming the connection parts and the wavy annular bodies.

In addition, while a balloon-expandable stent has been described in the embodiments above, the stent may be a self-expandable stent which has a self-expanding function.

The detailed description above describes features and aspects of embodiments of a stent disclosed here. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent comprising:
 a plurality of wavy annular bodies coaxially arranged in an axial direction so that adjacent wavy annular bodies are positioned axially adjacent one another;
 each wavy annular body including a plurality of circumferentially adjacent strut portions and a plurality of curved inflexed portions each connecting two of the strut portions which are circumferentially adjacent one another;
 the curved inflexed portions of each wavy annular body including crest-shaped curved inflexed portions and trough-shaped curved inflexed portions which are curved in opposite directions;
 a plurality of axially adjacent pairs of wavy annular bodies being connected to each other by connection parts, all of the connection parts connecting the plurality of axially adjacent pairs of wavy annular bodies being weaker than the wavy annular bodies allowing the connection parts to rupture in advance of the axially adjacent wavy annular bodies when a radially outwardly directed force is applied to the stent from inside the stent;
 each connection part having one end directly connected to a crest-shaped curved inflexed portion of one of the wavy annular bodies and an opposite end directly connected to a trough-shaped curved inflexed portion of the axially adjacent wavy annular body;
 each connection part extending in a slanting manner relative to the axial direction; and
 wherein the connection parts are first connection parts, and the stent further comprising, in addition to the plurality of wavy annular bodies, an endmost wavy annular body at each axial end of the stent, both of the endmost wavy annular bodies being connected to the axially adjacent wavy annular body by a second connection part possessing a greater width than the width of the first connection parts.

2. The stent according to claim 1, wherein each wavy annular body includes an area between circumferentially adjacent strut portions, the area between a first two of the circumferentially adjacent strut portions of each wavy annular body being different than the area between a second two of the circumferentially adjacent strut portions when the stent is radially outwardly expanded.

3. The stent according to claim 1, wherein the axially adjacent wavy annular bodies do not axially overlap one another.

4. The stent according to claim 1, wherein the connection parts possess a cross-sectional area smaller than the cross-sectional area of the wavy linear members forming the wavy annular bodies.

5. A stent comprising:
 a plurality of wavy annular bodies each comprised of a continuous wavy linear member, the wavy annular bodies being arranged in an axial direction;
 a plurality of connection parts each positioned between a pair of axially adjacent wavy annular bodies, each connection part interconnecting the pair of axially adjacent wavy annular bodies coaxially, all of the connection parts interconnecting the pair of axially adjacent wavy annular bodies being weaker than the pair of axially adjacent wavy annular bodies so that the connection part ruptures before the axially adjacent wavy annular bodies when a radially outwardly directed force is applied to the stent from inside the stent;
 each connection part extending in a slanting manner relative to the axial direction;

each connection part directly interconnecting one inflexed part of one wavy annular body which is curved to project toward an other wavy annular body positioned axially adjacent the one wavy annular body and an other inflexed part of the other wavy annular body which is curved to project toward the one wavy annular body; and wherein the connection parts are first connection parts, the stent further comprising, in addition to the plurality of wavy annular bodies, a first endmost wavy annular body at one axial end of the stent, and a second endmost wavy annular body at an opposite axial end of the stent, the first and second endmost wavy annular bodies being connected to an axially adjacent wavy annular body by a second connection part possessing a greater width than the width of the first connection parts.

6. The stent according to claim 5, wherein the one inflexed part has an inner edge portion curved in a shape projected toward the other wavy annular body, the other inflexed part has an inner edge portion curved in a shape projected toward the one wavy annular body, and the connection part extends parallel to a tangential line interconnecting the inner edge portion of the one inflexed part and the inner edge portion of the other inflexed part.

7. The stent according to claim 5, wherein the one inflexed part has an inner edge portion curved in a shape projected toward the other wavy annular body, the other inflexed part has an inner edge portion curved in a shape projected toward the one wavy annular body, and the connection part is located at a position spaced from a position on a tangential line interconnecting the inner edge portion of the one inflexed part and the inner edge portion of the other inflexed part.

8. The stent according to claim 5, wherein each connection part possesses a width smaller than the width of the wavy linear member.

9. A stent comprising:
a plurality of wavy annular bodies coaxially arranged in an axial direction so that adjacent wavy annular bodies are positioned axially adjacent one another;
the plurality of wavy annular bodies comprising first, second and third wavy annular bodies, the first and second wavy annular bodies being axially adjacent one another, the second and third wavy annular bodies being axially adjacent one another, and the second wavy annular body being axially between the first and third wavy annular bodies;
the first, second and third wavy annular bodies each including a plurality of circumferentially adjacent strut portions and a plurality of curved inflexed portions each connecting two of the strut portions which are circumferentially adjacent one another;
the curved inflexed portions of each wavy annular body including crest-shaped curved inflexed portions and trough-shaped curved inflexed portions which are curved in opposite directions;

the first and second wavy annular bodies being connected to each other by a plurality of circumferentially spaced apart connection parts which each possess one end directly connected to a crest-shaped curved inflexed portion of the second wavy annular body and an opposite end directly connected to a trough-shaped curved inflexed portion of the first wavy annular body, all of the connection parts connecting the first and second wavy annular bodies extending in a slanting manner relative to the axial direction;

the second and third wavy annular bodies being connected to each other by a plurality of circumferentially spaced apart connection parts which each possess one end directly connected to a crest-shaped curved inflexed portion of the third wavy annular body and an opposite end directly connected to a trough-shaped curved inflexed portion of the second wavy annular body, all of the connection parts connecting the second and third wavy annular bodies extending in a slanting manner relative to the axial direction;

all of the connection parts connecting the first and second wavy annular bodies, and all of the connection parts connecting the second and third wavy annular bodies, being weaker than the first, second and third wavy annular bodies, thus allowing the connection parts to rupture in advance of the first, second and third axially adjacent wavy annular bodies when a radially outwardly directed force is applied to the stent from inside the stent;

an axial endmost wavy annular body at both axial ends of the stent; and wherein the connection parts connecting the first and second wavy annular bodies, and the connection parts connecting the second and third wavy annular bodies, are first connection parts, wherein the plurality of wavy annular bodies includes a fourth wavy annular body and a fifth wavy annular body, the stent further comprising a plurality of second connection parts connecting the fourth wavy annular body to one of the axial endmost wavy annular body and connecting the fifth wavy annular body to the other axial endmost wavy annular body, the second connection parts connecting the fourth wavy annular body to the one axial endmost wavy annular body possessing a width greater than the width of the first connection parts, and the second connection parts connecting the fifth wavy annular body to the other axial endmost wavy annular body possessing a width greater than the width of the first connection parts.

* * * * *